United States Patent
Ahner et al.

(10) Patent No.: US 9,869,639 B2
(45) Date of Patent: *Jan. 16, 2018

(54) PHOTON EMITTER ARRAY INCLUDING PHOTON EMITTERS WITH DIFFERENT ORIENTATIONS

(71) Applicant: Seagate Technology LLC, Cupertino, CA (US)

(72) Inventors: Joachim Walter Ahner, Livermore, CA (US); David Marcus Tung, Livermore, CA (US)

(73) Assignee: Seagate Technology LLC, Cupertino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/364,548

(22) Filed: Nov. 30, 2016

(65) Prior Publication Data
US 2017/0082553 A1    Mar. 23, 2017

Related U.S. Application Data

(63) Continuation of application No. 14/194,443, filed on Feb. 28, 2014, now Pat. No. 9,581,554.
(Continued)

(51) Int. Cl.
*G01N 21/88* (2006.01)
*G01N 21/47* (2006.01)
*G01N 21/95* (2006.01)

(52) U.S. Cl.
CPC ......... *G01N 21/8806* (2013.01); *G01N 21/47* (2013.01); *G01N 21/4738* (2013.01);
(Continued)

(58) Field of Classification Search
CPC .. G01N 21/47; G01N 21/474; G01N 21/4738; G01N 21/4788; G01N 21/88;
(Continued)

(56) References Cited

U.S. PATENT DOCUMENTS

| 4,893,932 A | * | 1/1990 | Knollenberg | ...... G01N 21/9501 |
| | | | | 356/237.3 |
| 6,002,705 A | * | 12/1999 | Thornton | ................ H01S 5/423 |
| | | | | 372/103 |

(Continued)

FOREIGN PATENT DOCUMENTS

| JP | 2012234081 A | * | 11/2012 |
| JP | 2013213836 A | * | 10/2013 |

OTHER PUBLICATIONS

Machine Translation of 'Illumination Device and Optical Device' by Ogami Yohei; JP 20122234081 A published Nov. 29, 2012; 5 pages.*
(Continued)

*Primary Examiner* — Gordon J Stock, Jr.

(57) ABSTRACT

Provided herein is an apparatus including a photon emitter array. The photon emitter array includes a number of photon emitters selectively oriented in a number of polarized orientations. The photon emitters are configured to controllably emit photons onto a surface of an article. The apparatus also includes a photon detector positioned to receive photons scattered from features on the surface of the article. The photon detector simultaneously receives photons oriented in the number of polarized orientations. In addition, the photon detector provides information for mapping the features on the surface of the article.

7 Claims, 6 Drawing Sheets

Related U.S. Application Data (60) Provisional application No. 61/829,171, filed on May 30, 2013.

(52) U.S. Cl.
CPC ......... *G01N 21/95* (2013.01); *G01N 21/9506* (2013.01); *G01N 2021/8816* (2013.01); *G01N 2021/8845* (2013.01); *G01N 2021/8848* (2013.01)

(58) Field of Classification Search
CPC ........... G01N 21/8806; G01N 21/8851; G01N 21/95; G01N 21/9501; G01N 21/9506; G01N 21/956; G01N 21/95607; G01N 21/95623; G01N 21/21; G01N 21/25; G01N 21/8422; G01N 21/8901; G01N 2021/213; G01N 2021/4792; G01N 2021/8803; G01N 2021/8806; G01N 2021/8809; G01N 2021/8812; G01N 2021/8816; G01N 2021/8819; G01N 2021/8822; G01N 2021/8825; G01N 2021/8829; G01N 2021/8832; G01N 2021/8835; G01N 2021/8838; G01N 2021/8841; G01N 2021/8845; G01N 2021/8848; G01N 2021/8851; G01N 2021/8854; G01N 2021/8858; G01N 2021/8861; G01N 2021/8864; G01N 2021/8867; G01N 2021/887; G01N 2021/8874; G01N 2021/8877; G01N 2021/888; G01N 2021/8883; G01N 2021/8887; G01N 2021/889; G01N 2021/8893; G01N 2021/8896; G01N 2201/0612; G01N 2201/062; G01N 2021/4702; G01N 2021/4704; G01N 2021/4707; G01N 2021/4709; G01N 2021/4711; G01N 2021/4714; G01N 2021/4716; G01N 2021/4719; G01N 2021/4721; G01N 2021/4723; G01N 2021/4726; G01N 2021/4728; G01N 2021/473; G01N 2021/4733; G01N 2021/4735; G01N 2021/4742; G01N 2021/4745; G01N 2021/4747; G01N 2021/475; G01N 2021/4752; G01N 2021/4754; G01N 2021/4757; G01N 2021/4759; G01N 2021/4761; G01N 2021/4764; G01N 2021/4766; G01N 2021/4769; G01N 2021/4771; G01N 2021/4773; G01N 2021/4776; G01N 2021/4778; G01N 2021/478; G01N 2021/4783; G01N 2021/479; G01N 2021/4797

USPC .................. 356/364, 369, 370, 237.1–247.6, 356/238.1–240.1
See application file for complete search history.

(56) References Cited

U.S. PATENT DOCUMENTS

| | | | | |
|---|---|---|---|---|
| 6,166,393 | A * | 12/2000 | Paul | G01N 21/8901 250/559.08 |
| 6,324,203 | B1 * | 11/2001 | Owa | G03F 7/70025 372/106 |
| 7,319,229 | B2 * | 1/2008 | Vaez-Iravani | G02B 27/48 250/372 |
| 8,896,827 | B2 * | 11/2014 | Chimmalgi | G01N 21/8806 356/237.2 |
| 9,518,916 | B1 * | 12/2016 | Pandev | G01N 21/255 |
| 2004/0032581 | A1 * | 2/2004 | Nikoonahad | G01N 21/55 356/237.2 |
| 2008/0055897 | A1 * | 3/2008 | Yoshida | G02B 6/0068 362/231 |
| 2008/0297783 | A1 * | 12/2008 | Urano | G01N 21/9501 356/237.5 |
| 2009/0135434 | A1 * | 5/2009 | Keranen | B41F 33/0036 356/611 |
| 2013/0141730 | A1 * | 6/2013 | Quintanilha | G02B 6/10 356/446 |
| 2013/0301040 | A1 * | 11/2013 | Ahner | G01N 21/8851 356/237.2 |
| 2014/0043621 | A1 * | 2/2014 | Ahner | G01B 11/24 356/612 |
| 2014/0098364 | A1 * | 4/2014 | Ahner | G01N 21/63 356/237.2 |
| 2014/0098368 | A1 * | 4/2014 | Ahner | G01N 21/95 356/369 |
| 2014/0098370 | A1 * | 4/2014 | Ahner | G01N 21/4738 356/445 |
| 2014/0104604 | A1 * | 4/2014 | Ahner | G01N 21/95 356/237.4 |
| 2014/0152804 | A1 * | 6/2014 | Ahner | G06T 7/0004 348/92 |
| 2014/0160481 | A1 * | 6/2014 | Ahner | G01N 21/95 356/446 |
| 2015/0346083 | A1 * | 12/2015 | Matsumoto | G01N 21/8851 356/369 |
| 2015/0355554 | A1 * | 12/2015 | Mathijssen | G03F 9/7046 355/67 |
| 2016/0164258 | A1 * | 6/2016 | Weichmann | H01S 5/18355 382/154 |
| 2017/0125971 | A1 * | 5/2017 | Hiraga | H01S 5/022 |

OTHER PUBLICATIONS

SG Second Search Report and Written Opinion dated Mar. 7, 2017 in SG Application No. 11201509690U. 7 pages.

* cited by examiner

PHOTON EMITTER ARRAY INCLUDING PHOTON EMITTERS WITH DIFFERENT ORIENTATIONS

CROSS REFERENCE

This application is a continuation of prior application Ser. No. 14/194,443, filed Feb. 28, 2014, which claims the benefit of U.S. Provisional Patent Application No. 61/829,171, filed May 30, 2013.

BACKGROUND

An article fabricated on a production line may be inspected for certain features, including defects that might degrade the performance of the article or a system including the article. For example, a hard disk for a hard disk drive may be fabricated on a production line and inspected for certain surface features, including surface and subsurface defects that might degrade the performance of the disk or the hard disk drive. In some instances, inspection may be carried out with the use of an imaging apparatus that includes a camera and a light source to illuminate the article while the camera records images of the article. In such arrangements, it is appreciated that the light source may illuminate the article with randomly polarized light, and/or light polarized through a polarization filter, with insufficient intensity, which may result in some defects going undetected and consequently affect the performance of the article and/or a system including the article.

SUMMARY

Provided herein is an apparatus including a photon emitter array. The photon emitter array includes a number of photon emitters selectively oriented in a number of polarized orientations. The photon emitters are configured to controllably emit photons onto a surface of an article. The apparatus also includes a photon detector positioned to receive photons scattered from features on the surface of the article. The photon detector simultaneously receives photons oriented in the number of polarized orientations. In addition, the photon detector provides information for mapping the features on the surface of the article.

These and other features and aspects of the concepts provided herein may be better understood with reference to the following drawings, description, and appended claims.

DESCRIPTION

Before some particular embodiments are described and/or illustrated in greater detail, it should be understood by persons having ordinary skill in the art that the particular embodiments provided herein do not limit the concepts provided herein, as elements in such particular embodiments may vary. It should likewise be understood that a particular embodiment provided herein has elements which may be readily separated from the particular embodiment and optionally combined with or substituted for elements in any of several other embodiments described and/or illustrated herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art An article fabricated on a production line may be inspected for certain features, including defects, such as particle and stain contaminations, scratches and/or voids, that may degrade the performance of the article or a system including the article. It is appreciated that without inspecting an article for surface features, a finished surface of an article, such as a hard disk for a hard disk drive, may unknowingly be contaminated. Further, the contamination of the finished surface of an article may lead to scratch formation, debris generation, and/or corruption of the spacing between the hard disk and a read-write head.

To detect features on a surface of an article, optical inspection apparatus utilize high power light sources to irradiate the surface of the article. Although these high power light sources provide the desired intensity to irradiate an article, the light emitted is of a broad spectrum and of random polarization. Consequently, certain features that are responsive to, for instance, certain types of polarized light may go undetected. To overcome such issues, in some arrangements, a high power light source is coupled to an external polarization filter to filter the light and irradiate a light of a desired polarization on the surface of the article. However, a byproduct of such an arrangement is that the polarization filter diminishes the intensity of the light irradiated upon the article to an insufficient level for purposes of defect detection and analysis. As such, provided herein are embodiments to flexibly change polarization orientation of a photon emitter to emit photons of a specific polarization orientation without losing the intensity of the photons irradiated on a surface of an article.

In some embodiments described herein, an imaging apparatus includes a photon emitter array that includes steady-state photon emitters that can be customized to emit photons of a specific polarization orientation and/or wavelength. For instance, each of the photon emitters and/or a group of photon emitters of the photon emitter array may be configurable to change from one preselected polarization orientation to another preselected polarization orientation, may be selectively configured to emit photons of different wavelengths (e.g., colors, such as red, blue, green), and/or customizable based on some combination of polarization orientation and photon wavelengths. In this way, the embodiments described herein provide the flexibility to selectively customize polarization orientation and/or wavelength of photons to image a surface of an article for certain known defects and/or features that are known to scatter in a known manner with respect to a specific type of polarized photons and/or certain types of wavelengths, which would otherwise remain undetected. Furthermore, by utilizing a self-polarized photon emitter as described herein, features of an article can be detected, inspected and analyzed without losing the intensity with which the photons are irradiated on a surface of an article.

Figure 1:
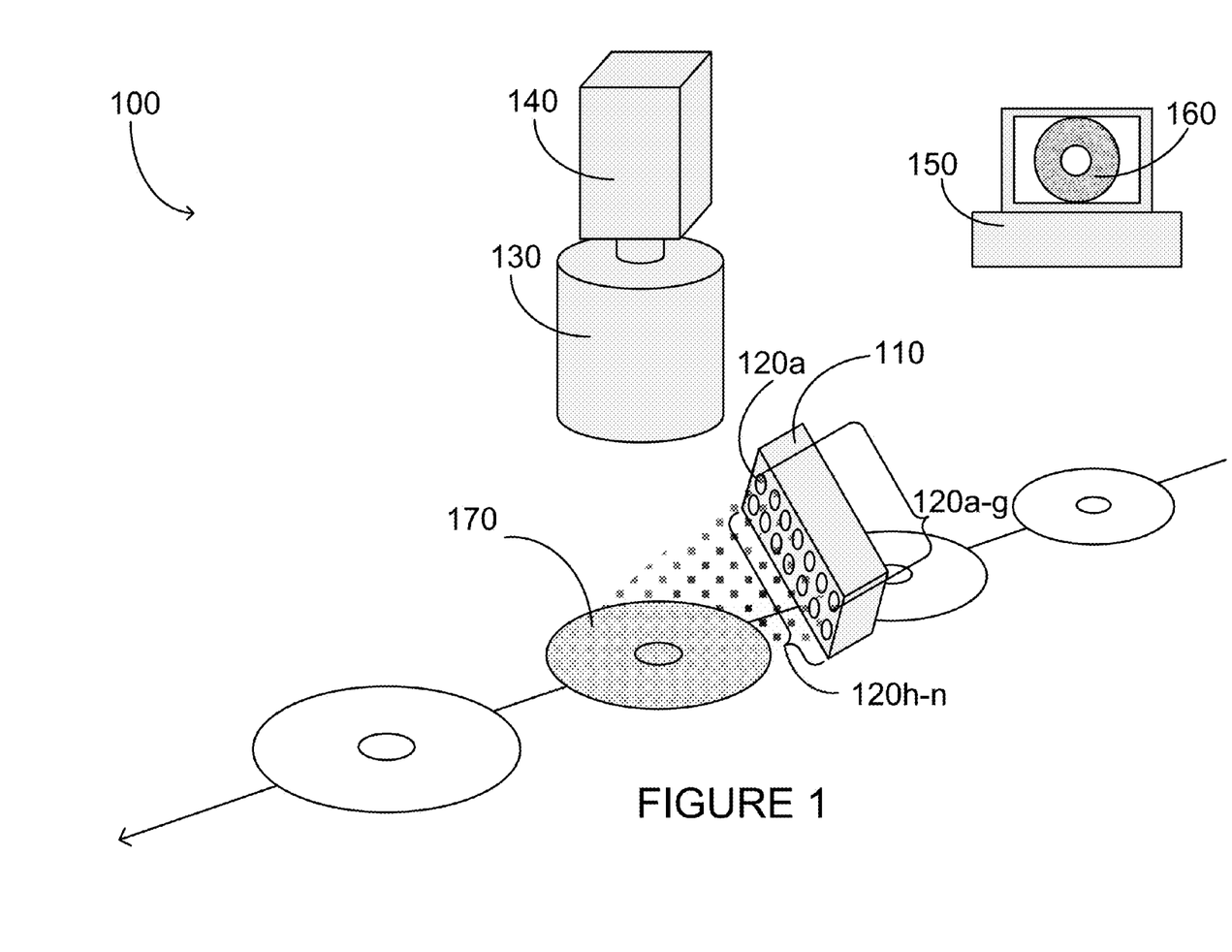
FIG. 1 shows an apparatus configured for surface feature detection and inspection of articles according to one aspect of the present embodiments.

FIG. 1 shows an apparatus configured for surface feature detection and inspection of articles according to one aspect of the present embodiments. Described in greater detail below, the apparatus 100 includes, but is not limited to, a two-dimensional photon emitter array 110 including photon emitters 120a-120n, an optical setup 130, a camera 140, and a computer 150 displaying an image 160 of article 170. It is appreciated that the apparatus described herein is illustrative and is not intended to limit the scope of the inventive concepts.

In some embodiments, detection and inspection of features of the article 170 may be performed by directing photons from photon emitters 120a-120n of preselected polarization orientations onto the surface of the article 170. When photons scatter from a location of a surface feature of the article 170, the optical setup 130 detects the scattered photons. The article 170 is imaged by the camera 140, surface features of the article 170 are mapped, and used to analyze the surface feature of the article 170.

Before proceeding to further describe the various components of apparatus 100, it is appreciated that the article 170 as described herein may be, but is not limited to, semiconductor wafers, magnetic recording media (e.g., hard disks for hard disk drives), glass blanks, workpieces having one or more optically smooth surfaces, and/or workpieces in any stage of manufacture.

Referring now to photon emitter array 110, in some embodiments, the photon emitter array 110 includes photon emitters 120a-120n arranged in parallel rows and columns that are configured to emit coherent and/or polarized photons onto the surface of the article 170. In some embodiments, the photon emitters 120a-120n of the photon emitter array 110 may be solid state diodes, such as lasers. For example, the photon emitters 120a-120n may be red (e.g., 635 nm), green (e.g., 532 nm), blue (e.g., 405 nm) lasers, and/or some combination thereof.

In some embodiments, the photon emitters 120a-120n of the photon emitter array 110 may be selectively oriented in different polarization orientations. In some instances, each individual photon emitter 120a-120n may be oriented in a different and unique polarization orientation from another photon emitter of the photon emitter array 110. That is, each photon emitter can be selectively oriented at different angles, such as at a 45°, 90°, 180°, and/or some other preselected angle, to irradiate the surface of the article 170 with photons of different polarization orientations. In some instances, groups of photon emitters 120a-120n of the photon emitter array 110 may be oriented with a certain polarization orientation. For example, one row of the photon emitter array 110 may be oriented at a first polarization orientation while another row of the photon emitter array 110 may oriented at a second polarization orientation. In another example, a few columns of photon emitters of the photon emitter array 110 may be of a first polarization orientation, another few columns of the photon emitters of the photon emitter array 110 may be arranged in a second polarization orientation, and the remaining few columns of the photon emitters 120a-120n of the photon emitter array 110 may be arranged in a third polarization orientation.

In some embodiments, the photon emitters 120a-120n of the photon emitter array 110 may be selectively changed to emit photons from one polarization orientation to another polarization orientation. For example, an image of the article 170 is recorded while photon emitter 120a emits photons onto the article 170 at a 45° polarization orientation. Then, the polarization orientation of the photon emitter 120a is changed to emit photons at, for instance, a 180° polarization orientation onto the surface of the article 170 to detect and record surface features of the article 170. It is appreciated that by changing the polarization orientations of the photons irradiated on the surface of the article 170, different types of surface features may be discriminated and inspected.

In some embodiments, as noted above, the photon emitters 120a-120n may be solid state diodes, such as lasers, that are configured to emit coherent and/or polarized photons. In such an embodiment, the diodes may be rotated into different angles to cause the photon emitters 120a-120n to emit photons of certain polarization orientations. In some instances, the lasers may be coupled in a known fashion to a laser beam shaper such that the combination of lasers and laser beam shaper emit photons onto the surface of article 170 at one or more polarization angles. This way, in this instance, the laser beam shaper may be used to adjust the angles of the laser to emit photons at one or more polarization orientations onto the surface of the article 170.

It is appreciated that the photon emitter array 110 described herein provides the flexibility to change the polarization orientation to detect specific types of surface features that are known to scatter in a known manner with respect to a specific type of polarized photons. Further, it is appreciated that by utilizing self-polarized photon emitters 120a-120n, features of an article can be detected and imaged without losing the intensity with which the photons are irradiated on a surface of an article as compared to the intensity of photons irradiated onto an article via an external polarization filter.

To provide further granularity in discriminating among different types of surface features, the photon emitters 120a-120n can be customized to emit photons of different wavelengths onto the surface of the article 170, in some embodiments. In some instances, each photon emitter 120a-120n may emit photons of a unique wavelength, such as photons of a violet wavelength, blue wavelength, green wavelength, red wavelength, and/or some other preselected wavelength, invisible as well as visible. In some instances, selected groups of photon emitters (e.g., 120a-120c) may emit photons of one wavelength while another group of photon emitters (e.g., 120f-120g and 120m-120n) of photon emitter array 110 may emit photons of a different wavelength.

Further, in some embodiments, the photon emitters 120a-120n may be selectively changed to emit photons from one wavelength to another wavelength. For example, as images of article 170 are recorded, the photon emitter 120a can be set up to emit photons of a red wavelength, then green wavelength, and then blue wavelength. As the example illustrates, the photon emitters 120a-120n of photon emitter array 110 may be set up to irradiate a surface of article 170 with photons of any predetermined sequence of photon wavelengths to discriminate among different types of surface features that are known to scatter in a known manner with respect to specific wavelengths.

It is further appreciated that the photon emitter array 110 provides the flexibility to arrange the photon emitters 120a-120n in different combinations of polarization orientations and wavelengths. This flexibility further allows a user to uniquely customize the photon emitter array 110 to emit photons on the surface of article 170 in a manner to expose and analyze surface features that are of interest.

In some embodiments, the photon emitters 120a-120n of photon emitter array 110 are arranged to simultaneously emit photons and irradiate the surface of the article 170, as illustrated in FIG. 1. In some embodiments, the photon emitters 120a-120n may be arranged to emit photons asynchronously. In some embodiments, the photon emitters 120a-120n may be arranged to emit photons, either simultaneously or asynchronously, based on the characteristic of the photon emitters 120a-120n. For example, some of the photon emitters 120a-120n may be selected to emit photons on the surface of the article 170 based on the polarization orientation of a photon emitter, the photon wavelength emitted by a photon emitter, or based on a combination of the polarization orientation and the photon wavelength of a photon emitter. In this way, different types of surface features may be detected and recorded for further feature analysis.

In some embodiments, the photon emitter array 110 may emit photons onto the entire surface as illustrated in FIG. 1 or some predetermined portion of the surface (e.g., for gradational rotation of the article for piecewise inspection, if desired) of the article 170. In some embodiments, it may be desirable to increase the number of photons (e.g., photon flux density) emitted from the photon emitters 120a-120n to provide an increase in photons scattered for detecting, mapping, and/or characterizing surface features of articles. Such an increase in photon flux density may be with respect to unit time for increased photon power, or with respect to unit area.

It is appreciated that the illustration of a single photon emitter array is an example, and is not intended to limit the scope of the inventive concepts described herein. In some embodiments, it is appreciated that more than one photon emitter array may be utilized to irradiate the surface of an article. It is further appreciated that the illustration of the photon emitters arranged in two rows and seven columns is illustrative and is not intended to limit the scope of the inventive concepts. For instance, the photon emitter array may include x rows by y columns of photon emitters, where x and y may be any number of rows and columns of photon emitters. In some instances, the photon emitters of a photon array, as well as pluralities of separate arrays, may be arranged in a circular shape, triangular shape, linearly, and/or in some other arrangement to facilitate the inspection and detection of features on the surface of an article.

It is further appreciated that the angle and position of the photon emitter array 110 illustrated in FIG. 1 is illustrative and is not intended to limit the scope of the embodiments. It is appreciated that the photon emitter array 110 may be positioned at any location around article 170. It is further appreciated that the angle of the photon emitter array 110 may be adjusted to emit photons onto the surface of an article to further detect and inspect specific surface features of the article known to scatter at those specific angles. The angle and position of the photon array 110 may also be adjusted to irradiate the entire surface or a predetermined portion of an article.

In some embodiments, the apparatus 100 includes an optical setup 130. The optical setup 130, in some embodiments, may be configured to manipulate photons emitted from the photon emitter array 110, reflected from the surface of the article 170 and/or scattered from the surface features of the article 170. For example, the optical setup 130 may include, but is not limited to, lenses, filters, gratings, and mirrors (not shown).

For instance, the optical setup 130 may include a lens coupled to a photon detector array (e.g., photon detector array 202 of FIG. 2) of camera 140 configured to collect and detect images of the surface features of the article 170. In this instance, the lens may have an entrance pupil and an exit pupil, and additional optical components (e.g., other lenses, gratings, and mirrors) may be positioned at or near the entrance pupil of the lens, at or near the exit pupil of the lens (e.g., in-between the exit pupil of the lens and the photon detector array), or some combination thereof to manipulate photons scattered from the surface features of the article 170. In some instances, the lens may be an objective lens, such as a telecentric lens, including an object-space telecentric lens (e.g., entrance pupil at infinity), an image-space telecentric lens (e.g., exit pupil at infinity), or a double telecentric lens (e.g., both pupils at infinity). Coupling a telecentric lens to a photon detector array reduces errors with respect to the mapped position of surface features of articles, reduces distortion of surface features of articles, and/or enables quantitative analysis of photons scattered from surface features of articles, which quantitative analysis includes integration of photon scattering intensity distribution for size determination of surface features of articles. It is appreciated that the optical setup 130 may include more than one lens.

In some embodiments, the optical setup 130 may include filters (not shown), such as a band-pass filter, a periodic array-tuned filter, and/or a phase filter. It is appreciated that one or more of these filters may be used to manipulate photons scattered from the surface features of the article 170 to distinguish between different types of surface features. In some embodiments, external filters, such as a band-pass filter, a periodic array-tuned filter, and/or a phase filter, may be used in conjunction with the photon emitter array 110 to manipulate photons emitted from the photon emitters 120a-120n prior to reaching the surface of the article 170. For example, a phase filter or waveplate may be used in conjunction with the photon emitter array 110 to emit photons on the surface of the article 170 to distinguish between surface features known to differentially scatter photons with respect to phase.

In some embodiments, the optical setup 130 may include mirrors. For example, the mirrors may be optical-grade mirror and/or one-way mirrors. In some embodiments, the mirrors may be used to manipulate photons reflected from the surface of the article 170, photons scattered from surface features of the article 170, and/or some combination thereof. In some embodiments, external mirrors may be used in apparatus 100 to manipulate photons emitted from the photon emitter array 110. For example, mirrors may be positioned in the apparatus 100 to redirect photons reflected off the surface of the article 170 back onto the surface of the article 170, thereby recycling photons that would otherwise be lost to the environment and minimizing the loss of the intensity of the photons irradiated on the surface of the article 170.

In some embodiments, the apparatus includes the camera 140 coupled to the optical setup 130 and communicatively coupled (not shown) to the computer 150. In some embodiments, the camera 140 may be configured to record images of the article 170 and transmit the recorded images to the computer 150 for processing and storage. The camera 140 may be a complementary metal-oxide semiconductor ("CMOS") camera, a scientific complementary metal-oxide semiconductor ("sCMOS") camera, a charge-coupled device ("CCD") camera, an electron-multiplying CCD ("EMCDD") camera, or a camera configured for use in feature detection and identification.

In some embodiments, the camera 140 may include a photon detector array (e.g., photon detector array 202 of FIG. 2) configured to collect and detect photons scattered from features on the surface of the article 170. The photon detector array (e.g., photon detector array 202 of FIG. 2) may comprise a complementary metal-oxide semiconductor ("CMOS"), a scientific complementary metal-oxide semiconductor ("sCMOS"), a charge-coupled device ("CCD"), or an electron-multiplying CCD ("EMCDD"), which may be part of the camera 140.

In some embodiments, depending upon factors that may include the type of article, the type of surface features (e.g., particle, stain, scratch, void, etc.), and the like, it may be desirable at times to increase detection time of the photon detector array (e.g., photon detector array 202 of FIG. 2) of the camera 140 to detect more photons for detecting, mapping, and/or characterizing surface features of articles. In some embodiments, for example, detection time may be increased to detect more photons. In such embodiments, a CCD-based photon detector array, including an electron-multiplying EMCCD may be used to further detect more photons.

In some embodiments, the photon detector array and/or camera 140 may be oriented to collect and detect photons scattered from surface features of the article 170 at an optimized distance and/or an optimized angle for a maximum acceptance of scattered photons from one or more types of surface features. Such an optimized angle may be the angle between a ray (e.g., a photon or light ray) including the center line axis of the photon detector array to the surface of the article 170 and the normal (i.e., a line perpendicular to the surface of the article 170) at the point at which the ray is extended. The optimized angle may be equal to or otherwise include a scatter angle for one or more types of surface features, and the scatter angle may be a different angle than the angle of reflection, which angle of reflection is equal to the angle of incidence. For example, photon detector array and/or the camera 140 may be oriented at an optimized angle ranging from 0° to 90°. Here, an optimized angle of 90° represents orientation of the photon detector array and/or camera 140 at a side of the article 170, an optimized angle of 0° represents orientation of the photon detector array or photon detector array directly above the article 170, as illustrated in FIG. 1.

Although FIG. 1 illustrates a single camera with a single photon detector array, it is intended to be illustrative and is not intended to limit the scope of the inventive concepts described herein. In some embodiments, the apparatus 100 may comprise a plurality of cameras including a plurality of photon detector arrays. In other embodiments, the apparatus 100 may include a plurality of cameras, where each camera includes a single photon detector array. In further embodiments, the apparatus 100 may include a single camera including a plurality of photon detector arrays.

In some embodiments, the apparatus 100 further includes the computer 150. The computer 150 may be communicatively coupled to the camera 140 (not shown for clarity of illustration) to store images of the article 170 recorded by the camera 140. In some embodiments, the computer 150 may be communicatively coupled (not shown) to the photon emitter array 110 to control how photons are emitted onto the surface of the article 170. For instance, the computer 150 may be configured to select and change the polarization orientations of the photon emitters 120a-120n, and select and change the wavelength of the photons emitted from the photon emitters 120a-120n. In some instances, the computer 150 may be configured to move the photon emitter array 110 to a distance and/or an angle optimized for inspecting one or more types of features, switch the photon emitter array 110 on and/or off, and/or switch between modes for emitting photons and not emitting photons. Further, in some instances, the computer 150 may be configured to cause the photon emitters 120a-120n to emit photons simultaneously, asynchronously, based on characteristics of the photon emitters 120a-120n (e.g., polarization orientation, wavelength, and/or some combination thereof), or based on some other sequence.

Computer 150 may also be configured to, but is not limited to, mount and unmount the article 170 in the apparatus 100, position the article 170 for illumination and inspection by maintaining the position of the article 170 in the apparatus 100, and/or optionally including gradational rotation of the article 170 for piecewise inspection. In some embodiments, the computer 150 may be configured to insert optical components into the optical setup 130, for example, using a mechanical actuator, position optical components for inspection, adjust optical components (e.g., focus lenses) and/or tune optical components for inspection, and/or remove optical components from the optical setup 130.

In some embodiments, the computer 150 may be further configured to identify features of the article 170, such as disk defects. For instance, the computer 150 may be configured to process photon detector array (e.g., photon detector array 202 of FIG. 2) signals from scattered photons, including pixel interpolation for better accuracy (e.g., 10$x$ better than pixel size) with respect to the position of surface features. In some embodiments, the computer 150 may be configured to synchronize each photon emitter of photon emitter array 110 with each pixel sensor (e.g., pixel sensor 204 of FIG. 2) of a photon detector array (e.g., photon detector array 202 of FIG. 2) in accordance with a photon emission-photon detection scheme.

In some instances, the computer 150 may map or otherwise determine the position of surface features of articles from photon detector array signals or processed photon detector array signals. For example, the computer 150 may be operable to accurately and/or precisely determine the photon scattering intensity distribution (e.g., FIGS. 5A [bottom] and 5B [bottom]) of a feature on the surface of an article. Such a photon scattering intensity distribution may be used to characterize a surface feature of an article both quantitatively and qualitatively.

As noted above, the computer 150 may quantitatively and/or qualitatively characterize surface features of articles, in some instances. With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a number of articles and be used to correct manufacturing trends should such features include surface and/or subsurface defects that might degrade the performance of the article.

With respect to qualitative characterization of a surface feature of an article, qualitative characterization may include a determination of the morphology, form, or shape of the surface feature of the article, including whether the surface feature is a particle, a stain, a scratch, or a void, etc., which determination may be effected by, but is not limited to, analysis of photon scattering intensity distributions. Qualitative characterization may further include chemical characterization of surface features known to differentially scatter photons such as, but not limited to, certain oxides, which may have faceted surfaces that differentially and/or directionally scatter photons. Qualitative characterization may even further include distinguishing between surface features known to differentially scatter photons with respect to wavelength, polarization orientation of a photon emitter of a photon emitter array, and/or a phase filter or a waveplate.

In some embodiments, qualitative characterization of one or more surface features of an article may include contrasting photon-scattering information in the effective absence of one of the photon emitter characteristics (e.g., photon wavelength, polarization orientation) with photon-scattering information using one or more of the foregoing photon emitter characteristics or contrasting a first surface features map produced in the effective absence of one of the foregoing photon emitter characteristics with a second surface features map (or a number of surface features maps) produced using one or more of the photon emitter characteristics. Along with quantitative characterization information, such qualitative characterization information may be cataloged across a number of articles and be used to correct manufacturing trends should such features include surface and/or subsurface defects that might degrade the performance of the article.

It is appreciated that computer 150 may be a desktop computer, a workstation, a portable device (e.g., a mobile device, a tablet, a laptop, or a smartphone), a server or some computing device that may be configured to store and perform image based feature detection and inspection.

It is appreciated that the apparatus 100 described herein may be configured to process or inspect articles at a rate greater than or commensurate with the rate at which the articles or workpieces thereof are produced. Processing or inspecting articles at rates greater than or commensurate with the rate at which the articles or workpieces thereof are produced is a function of many features of the apparatus 100 described herein, including, but not limited to, photon emitters, photon emitter arrays, and/or articles that need not be moved (e.g., for scanning) during processing or inspecting. For example, with photon emitter array 110, an article such as a hard disk of a hard disk drive need not be rotated during processing or inspecting. As such, the apparatus 100 can hold an article stationary while emitting photons onto the surface of the article, thereby saving time since the article can be quickly examined while remaining in a static position.

Figure 2:
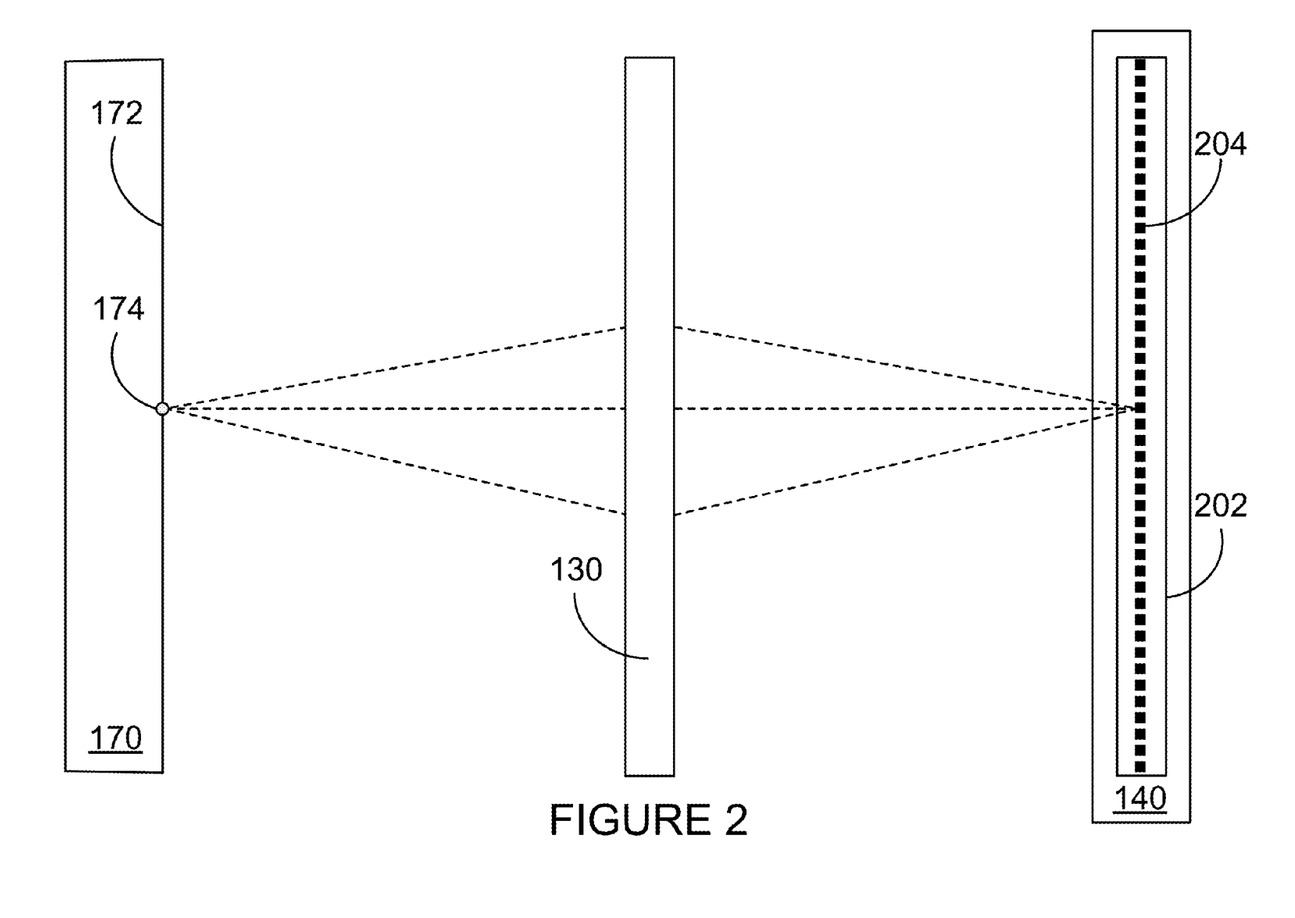
FIG. 2 illustrates a schematic of photons scattering from a surface feature of an article, through an optical set up, and onto a photon detector array according to one aspect of the present embodiments.

Referring now to FIG. 2, a schematic of photons scattering from a surface feature of an article, through an optical set up, and onto a photon detector array is illustrated according to one aspect of the present embodiments. As illustrated in FIG. 2, article 170 comprises a surface 172 and a surface feature 174. Although FIG. 2 illustrates an article with a single surface feature, it is intended to be an example and not intended to limit the scope of the inventive concepts. It is appreciated that an article may have more than one feature, which may be imaged for feature detection, identification and/or feature analysis.

Photons emitted from a photon emitter array, such as photon emitter array 110 of FIG. 1, or a plurality of photon emitter arrays may be scattered by the surface feature 174 and collected and detected by the optical setup 130 in combination with photon detector array 202 of camera 140, which may be positioned at a distance and/or an angle for an optimum acceptance of photons (e.g., maximum acceptance of photons with minimum background noise) scattered from one or more types of features.

The optical setup 130, which may comprise a telecentric lens, may collect and focus the photons scattered from the surface feature 174 onto one or more pixel sensors 204 of photon detector array 202, which each may comprise a photon detector coupled to an amplifier (e.g., CMOS/sC-MOS-based photon detector array). The one or more pixel sensors 204, each of which corresponds to a particular, fixed area of an article's 170 surface 172 and a pixel in a map of the article's 170 surface features, may provide one or more signals to a computer, such as computer 150 described in FIG. 1, for mapping or otherwise determining the position of the surface feature 174.

Figure 3:
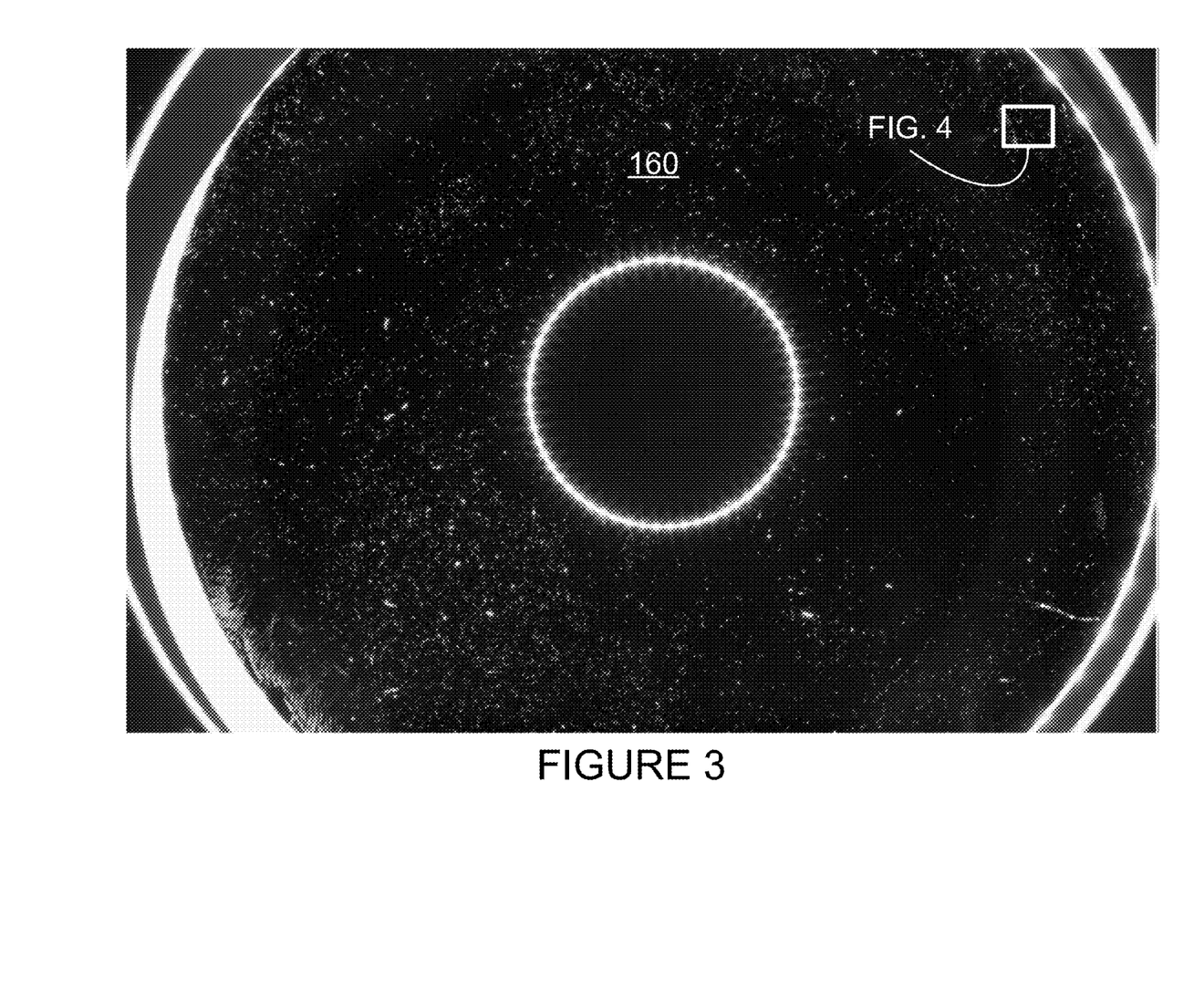
FIG. 3 shows a close-up partial map of surface features of an article inspected for surface features according to one aspect of the present embodiments.
Figure 4:
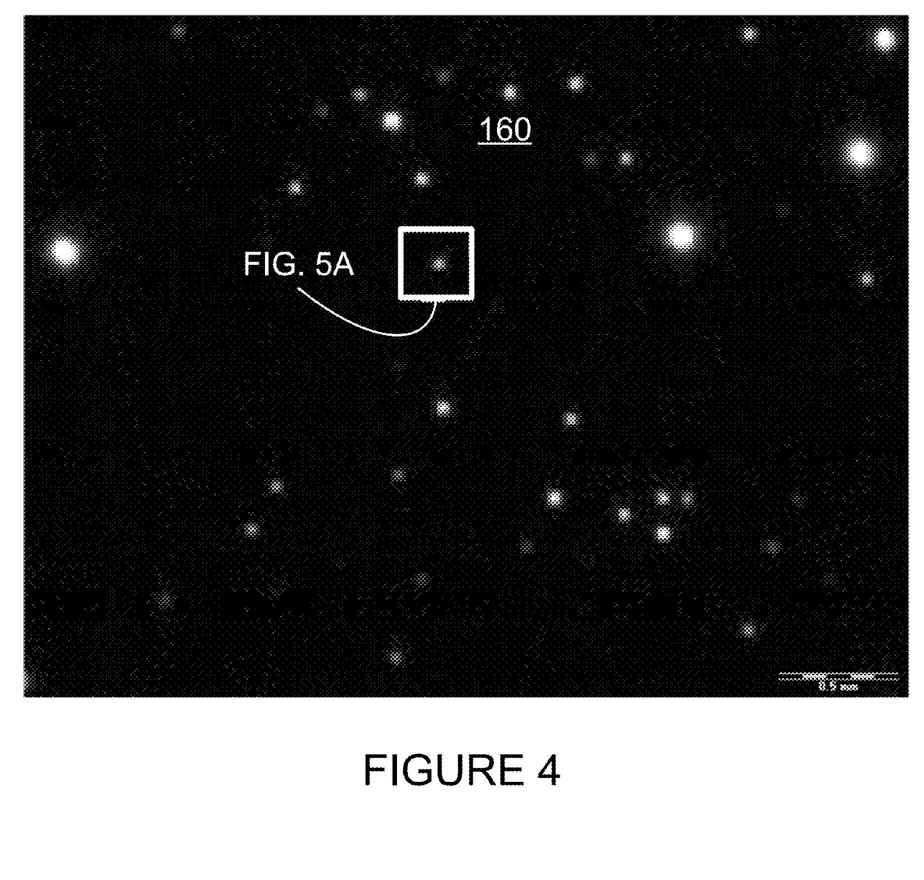
FIG. 4 provides a close-up image of a portion of the surface features map shown in FIG. 3, according to one aspect of the present embodiments.
Figure 5A:
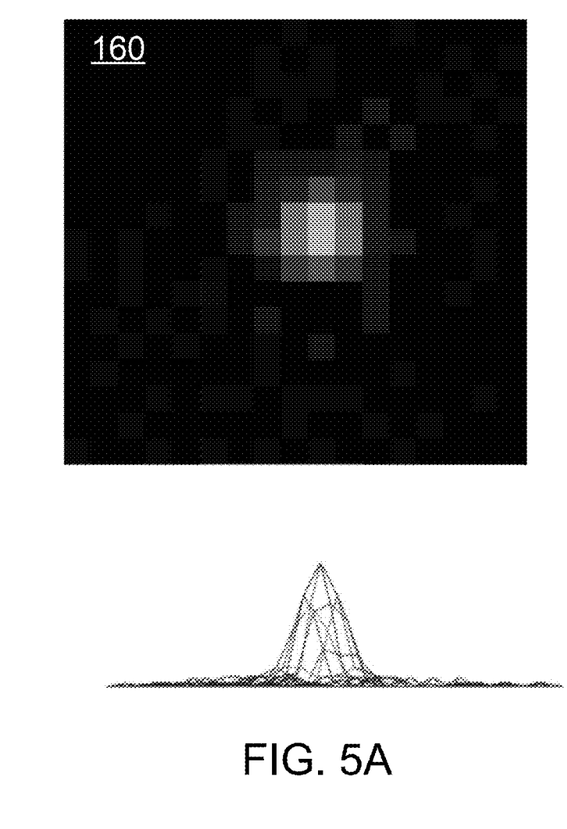
FIG. 5A (top) provides an illustrative example of a close-up image of the corresponding surface feature from the surface features map provided in FIG. 4, and FIG. 5A (bottom) provides a photon scattering intensity distribution of the surface feature, according to aspects of the present embodiments.
Figure 5B:
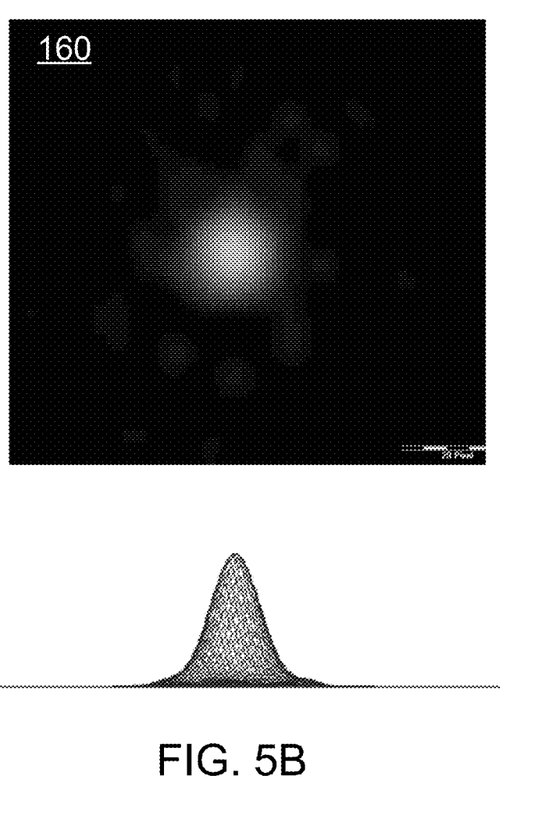
FIG. 5B (top) provides a close-up, pixel-interpolated image of the surface feature depicted in FIG. 5A, and FIG. 5B (bottom) provides a photon scattering intensity distribution of the pixel-interpolated surface feature, according to aspects of the present embodiments.

FIG. 5A provides an illustrative example of a close-up image of the map of surface features provided in FIG. 4, which, in turn, is an illustrative example of a close-up image of the map of surface features provided in FIG. 3. A computer, such as computer 150 of FIG. 1, or equivalent device may subsequently use pixel interpolation for further mapping the surface feature 174. FIG. 5B provides an illustrative example of a pixel-interpolated image of a surface feature, such as a surface feature from FIG. 5A. Although FIGS. 3-4 and FIGS. 5A-5B depict images of a magnetic medium, it is appreciated that the depictions are illustrative and are not intended to limit the scope of the inventive concepts described herein. It is appreciated that the imaging, and mapping, pixel interpolation as illustrated in FIGS. 3-4 and FIGS. 5A-5B may be used for articles in different stages of manufacture.

Figure 6:
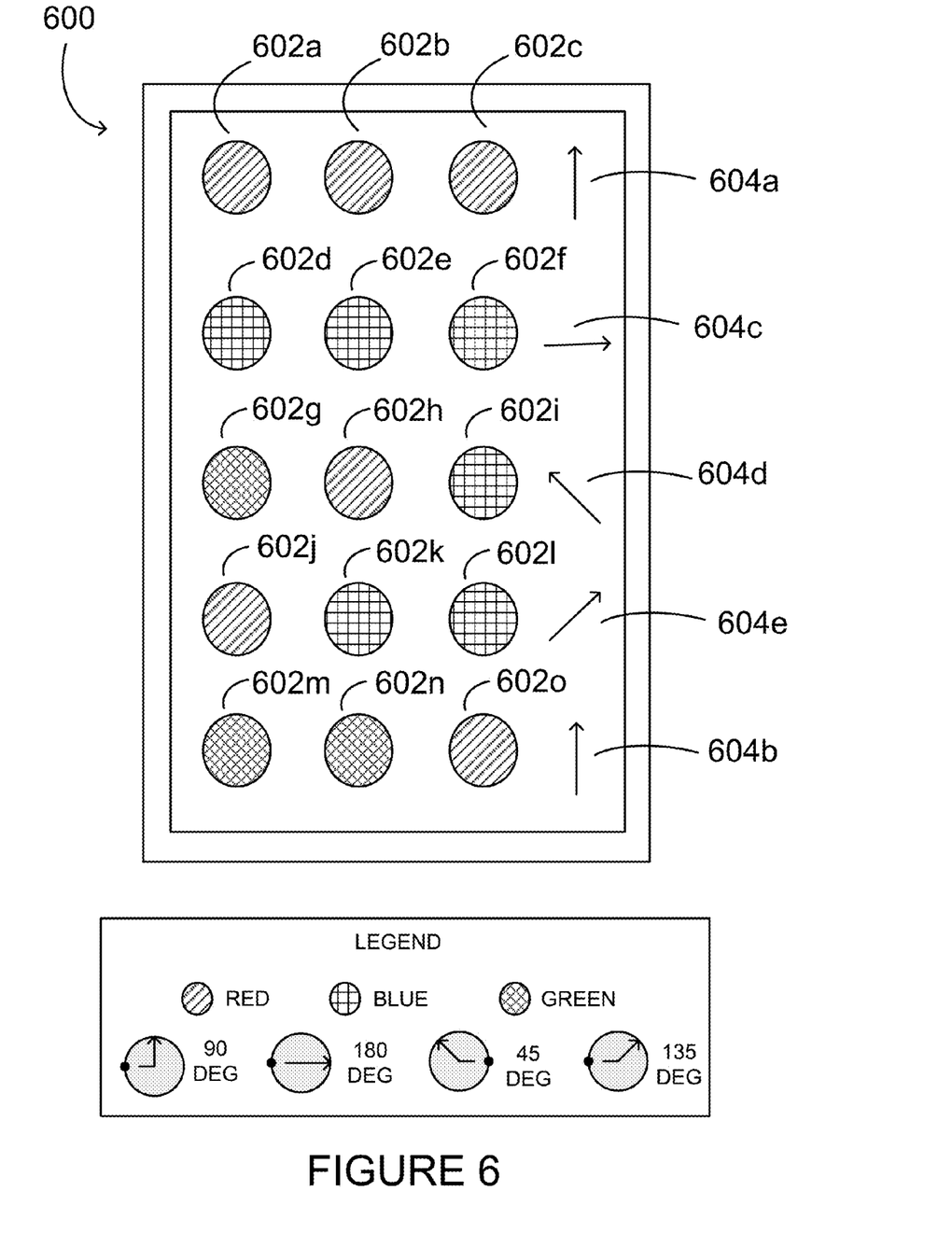
FIG. 6 shows a photon emitter array according to one aspect of the present embodiments.

Referring now to FIG. 6, a photon emitter array is shown according to one aspect of the present embodiments. Photon emitter array 600 is substantially similar to the photon emitter array 110 of FIG. 1. It is further appreciated that the photon emitter array 600 may be used in conjunction with an apparatus configured to inspect and detect surface features of articles, such as apparatus 100.

The photon emitter array 600 is a two-dimensional array including five rows and three columns of photon emitters 602a-602o configured to emit photons on a surface of an article, such as article 170 of FIG. 1. Photon emitters 602a-602o are substantially similar to the photon emitters 120a-120n of FIG. 1.

Similar to photon emitters 120a-120n, the photon emitters 602a-602o are configured to emit coherent and polarized photons onto a surface of an article. In this embodiment, the photon emitters 602a-602o are oriented in different polarization orientations to detect and inspect different types of surface features of an article that are known to scatter in a known manner with respect to specific polarization orientations. Here, for instance, photon emitters 602a-602c and 602m-602o are oriented at 90° angles, which is indicated by arrows 604a and 604b, respectively. While photon emitters 602d-602f are oriented at 180° angles, indicated by arrow 604c, and photon emitters 602g-602i and 602j-602l are oriented at 45° angles and 135° angles, as indicated by arrows 604d and 604e, respectively. In such a polarization orientation arrangement, specific types of defects and surface features of an article may be exposed and inspected that are known to scatter when photons of polarization orientations of 45°, 90°, 135°, and 180° are irradiated on a surface of an article.

It is appreciated that the polarization orientations illustrated in FIG. 6 are examples and not intended to limit the inventive concepts described herein. As similarly noted with respect to FIG. 1, photon emitters 602a-602o may have the same polarization orientations, unique polarization orientations, groups of the same polarization orientations, and/or some other polarization orientation arrangement. It is also appreciated that the polarization orientations of the photon emitters 602a-602o need not be static, and may be changed from one polarization orientation to another polarization orientation by rotating the photon emitters 602a-602o from one angle to another angle. For example, photon emitter 602g may be rotated from 45° angle to 48° angle, and then further rotated to 100°.

It is also appreciated that by utilizing self-polarized photon emitters, such as photo emitters 602a-602o, the intensity of the photons irradiated on a surface of an article is greater than using, for instance, an external polarization filter in conjunction with the photon emitters to emit photons on a surface of an article. In this way, the use of self-polarized photon emitters improves the detection and inspection of features that would otherwise go undetected.

Further, in this embodiment, the photon emitters 602a-602o may be configured to emit photons of different wavelengths to expose and detect specific features of an article known to scatter in a known manner with respect to the specific wavelengths. For instance, the photon emitters 602a-602o emit red (e.g., 650 nm), blue (e.g., 475 nm) and green (e.g., 510 nm) colored photons. Also, in this exemplary embodiment, some of the rows of photon emitters are arranged to emit photons of the same wavelength (e.g., photon emitters 602a-602c and 602d-602f), while other rows of photon emitters are arranged to emit photons of different wavelengths (e.g., photons 602g-602i, 602j-602l and 602m-602o).

However, it is appreciated that the photon emitters 602a-602o may be arranged to emit photons of different wavelengths than the one illustrated in FIG. 6. For instance, instead of emitting red, blue and green photons, the photon emitters 602a-602o may emit yellow, violet, or some other wavelength of visible light. It is further appreciated that photon emitters may emit photons of a relatively wide range of wavelengths (e.g., whole spectrum, broad spectrum, ultraviolet, infrared, etc.). Further, as noted in FIG. 1, each of the photon emitters 602a-602o may be configured and then reconfigured to emit photons of different wavelengths. Furthermore, in some instances as noted in FIG. 1, the photon emitters 602a-602o may all be configured to emit photons of the same wavelength, photons of a unique wavelength, groups of photon emitters emitting the same wavelength, and/or some other wavelength arrangement.

It is further appreciated that being able to selectively configure the polarization orientation of the photon emitters and/or configure the wavelength of the photons emitted from the photon emitters, the photon emitter array 600 may be arranged in many different permutations to emit and irradiate a surface of an article, thereby resulting in exposure and detection of different types of surface features.

In some embodiments, the photon emitter array 600 may be configured to emit photons simultaneously. For instance, all of the photon emitters 602a-602o may emit photons at the same time to irradiate a surface of an article that is being inspected for surface features. In some instances, the photon emitters 602a-602o may emit photons simultaneously based on a photon emitter characteristic. For instance, photon emitters 602a-602o may all be configured to emit photons of predetermined wavelength in order of a predetermined sequence. For example, the photon emitters 602a-602o may all emit red colored photons, then blue colored photons, and then violet colored photons. In some instances, the photon emitters 602a-602o may all be configured to emit photons of a predetermined polarization orientation sequence, such as at 10° angles, then 50° angles, and then at 110° angles. In some instances, the photon emitters 602a-602o may all emit photons in a sequence based on a combination of photon wavelength and polarization orientation sequence. For example, the photon emitters 602a-602o may emit red color photons at 15° angle, then emit green colored photons at an 80° angle, and then emit green colored photons at a 45° angle.

In some embodiments, the photon emitters 602a-602o may be configured to emit photons asynchronously. In some instances, the photon emitters may be configured to emit photons asynchronously based on a photon emitter characteristic. For instance, the photon emitter array 600 may be configured to cause the photon emitters 602a-602o to emit photons based on a polarization orientation sequence. For example, first the photon emitters oriented at 90° angle may emit photons (e.g., photon emitters 602a-602c and 602m-602o), then photon emitters oriented at a 45° angle may emit photons (e.g., photon emitters 602g-602i), and then photon emitters oriented at 135° angle (e.g., photon emitters 602j-602l) may emit photons. In some instances, the photon emitter array 600 may be configured to cause photon emitters 602a-602o to emit photons based on a photon wavelength sequence. For example, initially, photon emitters that are configured to emit green colored photon emit photons (e.g., photon emitters 602g and 602n), then red colored photons (e.g., photon emitters 602a-602c, 602h, 602j and 602o), and then blue colored photons (e.g., photon emitters 602d-602f, 602i and 602k-602l). In yet some instances, the photon emitter 600 may be configured to emit photons in a sequence based on a combination of photon wavelength and polarization orientation of a photon emitter.

In some embodiments, the photon emitters 602a-602o may be manually configured to emit photons at a specific polarization orientation, to emit photons of a certain wavelength, and/or some combination thereof. However, in some other embodiments, the photon emitter array 600 may be communicatively coupled to a computer, such as computer 150, that may automatically configure and re-configure the photon emitters 602a-602o to emit photons of a specific polarization, photon wavelength, and/or some combination thereof.

As such, provided herein is an apparatus, including a photon emitter array comprising a plurality of photon emitters configured to emit coherent and polarized photons onto a surface of an article, a photon detector configured to receive photons scattered from features on the surface of the article, and a mapping means for mapping the features on the surface of the article based on information received from the photon detector.

In some embodiments, one photon emitter of the plurality of photon emitters is configured to emit photons of a first wavelength and another photon emitter of the plurality of photon emitters is configured to emit photons of a second wavelength. The first and second wavelengths are different, in some embodiments. In some embodiments, the plurality of photon emitters is configured to selectively change the emitted photons from one polarization orientation to another polarization orientation.

In some embodiments, at least one of the photon emitters is a solid state diode. In some embodiments, one photon emitter of the plurality of photon emitters is arranged in parallel with respect to another photon emitter of the plurality of photon emitters. In some embodiments, the apparatus further includes a telecentric lens coupled to the photon detector. In some embodiments, the photon detector comprises a complementary metal-oxide semiconductor ("CMOS"), a scientific complementary metal-oxide semiconductor ("sCMOS"), or a charge-coupled device ("CCD").

Also provided herein is an apparatus, including a photon emitter array comprising a plurality of photon emitters selectively oriented in a plurality of polarized orientations and configured to controllably emit photons onto a surface of an article, a photon detector configured to receive photons scattered from features on the surface of the article, and a mapping means for mapping the features on the surface of the article based on information received from the photon detector.

In some embodiments, the plurality of photon emitters is configured to selectively change the emitted photons from one orientation to another orientation of the plurality of polarized orientations. In some embodiments, one photon emitter of the plurality of photon emitters is configured to emit photons of a first wavelength and another photon emitter of the plurality of photon emitters is configured to emit photons of a second wavelength. The first and second wavelengths are different, in some embodiments. In some embodiments, the plurality of photon emitters is configured to emit photons simultaneously. The plurality of photon emitters is configured to emit photons asynchronously based on a photon emitter characteristic, in some embodiments. In some embodiments, the photon emitter characteristic includes a polarization orientation of a photon emitter of the plurality of photon emitters, photon wavelength emitted by the photon emitter, or a combination of the polarization orientation and the photon wavelength.

Also provided herein is an apparatus including at least two photon emitters, each with a preselected polarization orientation, and configured to emit polarized photons onto a surface of an article, and a processing means configured to process photon-detector signals corresponding to photons scattered from surface features of the article, and generate one or more surface features maps for the article from the photon-detector signals corresponding to the photons scattered from the surface features of the article.

In some embodiments, the photon emitters are configured to selectively change the emitted photons from one polarization orientation to another polarization orientation. In some embodiments, one photon emitter of the at least two photon emitters is configured to emit photons of a first wavelength and another photon emitter of the at least two photon emitters is configured to emit photons of a second wavelength. The first and second wavelengths are different, in some embodiments. In some embodiments, the at least two photon emitters are configured to emit photons asynchronously based on a photon emitter characteristic. In some embodiments, the photon emitter characteristic includes a polarization orientation of a photon emitter of the at least two photon emitters, photon wavelength emitted by the photon emitter, or a combination of the polarization orientation and the photon wavelength.

In some embodiments, the apparatus further includes a photon emitter array comprising a plurality of photon emitters, wherein the plurality of photon emitters include the at least two photon emitters. In some embodiments, the apparatus further includes a photon detector configured to receive photons scattered from features on the surface of the article and transmit photon-detector signals to the processing means. The photon detector comprises a complementary metal-oxide semiconductor ("CMOS"), a scientific complementary metal-oxide semiconductor ("sCMOS"), or a charge-coupled device ("CCD"), in some embodiments.

While some particular embodiments have been described and/or illustrated herein, and while these particular embodiments have been described and/or illustrated in considerable detail, it is not the intention of the applicants for these particular embodiments to limit the scope of the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts provided herein. The implementations provided herein and other implementations are within the scope of the following claims.

What is claimed is:

1. An apparatus comprising:
   a photon emitter array comprising
      a first plurality of photon emitters configured to emit coherent and polarized photons oriented at a first polarization orientation onto a location of a surface of an article, and
      a second plurality of photon emitters configured to emit coherent and polarized photons oriented at a second polarization orientation onto the surface of the article, wherein the second plurality of photon emitters emit onto the same location of the surface as the first plurality of photon emitters; and
   a photon detector configured to receive photons scattered from features on the surface of the article, wherein the photon detector provides information for mapping the features on the surface of the article.

2. The apparatus of claim 1, wherein:
   one photon emitter of the first plurality of photon emitters is configured to emit photons of a first wavelength and another photon emitter of the second plurality of photon emitters is configured to emit photons of a second wavelength; and the first and second wavelengths are different.

3. The apparatus of claim 1, wherein the first plurality of photon emitters is configured to selectively change the emitted photons from one polarization orientation to another polarization orientation.

4. The apparatus of claim 1, wherein at least one of the first plurality of photon emitters or one of the second plurality of photon emitters is a solid state diode.

5. The apparatus of claim 1, wherein one photon emitter of the first plurality of photon emitters is arranged in parallel with respect to another photon emitter of the first plurality of photon emitters.

6. The apparatus of claim 1 further comprising a telecentric lens coupled to the photon detector.

7. The apparatus of claim 1, wherein the photon detector comprises a complementary metal-oxide semiconductor ("CMOS"), a scientific complementary metal-oxide semiconductor ("sCMOS"), or a charge-coupled device ("CCD").

* * * * *